(12) United States Patent
Axtell et al.

(10) Patent No.: US 7,256,156 B2
(45) Date of Patent: *Aug. 14, 2007

(54) REACTIVE-ADSORPTIVE PROTECTIVE MATERIALS AND METHODS FOR USE

(75) Inventors: Holly C. Axtell, Factoryville, PA (US); Scott M. Hartley, Clarks Summit, PA (US); Robert A. Sallavanti, Dalton, PA (US)

(73) Assignee: Gentex Corporation, Carbondale, PA (US)

( * ) Notice: Subject to any disclaimer, the term of this patent is extended or adjusted under 35 U.S.C. 154(b) by 381 days.

This patent is subject to a terminal disclaimer.

(21) Appl. No.: 10/372,352

(22) Filed: Feb. 24, 2003

(65) Prior Publication Data

US 2003/0220195 A1 Nov. 27, 2003

Related U.S. Application Data

(60) Provisional application No. 60/360,050, filed on Feb. 25, 2002.

(51) Int. Cl.
*C01B 31/08* (2006.01)
(52) U.S. Cl. ..................................... 502/417
(58) Field of Classification Search ................ 502/417; 428/408
See application file for complete search history.

(56) References Cited

U.S. PATENT DOCUMENTS

| | | | |
|---|---|---|---|
| 4,242,226 A | 12/1980 | Siren | |
| 4,397,907 A | 8/1983 | Rosser et al. | |
| 4,569,895 A | 2/1986 | Willett et al. | |
| 4,610,905 A | 9/1986 | von Blucher et al. | |
| 4,797,318 A | 1/1989 | Brooker et al. | |
| 4,831,011 A | 5/1989 | Oikawa et al. | |
| 5,014,355 A | 5/1991 | Vollenweider, II | |
| 5,032,209 A | 7/1991 | Shinbach et al. | |
| 5,092,008 A | 3/1992 | Okubo | |
| 5,482,773 A | 1/1996 | Bair | |
| 5,486,410 A | 1/1996 | Groeger et al. | |
| 5,582,913 A | 12/1996 | Simons | |
| 5,620,643 A | 4/1997 | Maiden et al. | |
| 5,639,307 A | 6/1997 | Bellemare | |
| 5,690,705 A | 11/1997 | Holmes et al. | |
| 5,712,219 A | 1/1998 | Klabunde et al. | |
| 5,736,473 A | 4/1998 | Cohen et al. | |
| 5,759,939 A | 6/1998 | Klabunde et al. | |
| 5,914,436 A | 6/1999 | Klabunde et al. | |
| 5,952,125 A | 9/1999 | Bi et al. | |
| 5,962,082 A | 10/1999 | Hendrickson et al. | |
| 5,972,808 A | 10/1999 | Groeger et al. | |
| 5,989,514 A | 11/1999 | Bi et al. | |
| 5,990,348 A | 11/1999 | Lyons et al. | |
| 5,990,373 A | 11/1999 | Klabunde | |
| 6,024,813 A | 2/2000 | Groeger et al. | |
| 6,037,019 A | 3/2000 | Kooyer et al. | |
| 6,043,184 A | 3/2000 | Karmakar et al. | |
| 6,045,650 A | 4/2000 | Mitchnick et al. | |
| 6,057,488 A | 5/2000 | Koper et al. | |
| 6,060,419 A | 5/2000 | Wijesekera et al. | |
| 6,074,437 A | 6/2000 | Racheria et al. | |
| 6,087,294 A | 7/2000 | Klabunde et al. | |
| 6,093,236 A | 7/2000 | Klabunde et al. | |
| 6,113,807 A | 9/2000 | Yamaura et al. | |
| 6,169,202 B1 | 1/2001 | Wijesekera et al. | |
| 6,184,177 B1* | 2/2001 | von Blucher et al. | 502/434 |
| 6,235,673 B1 | 5/2001 | Zoeller et al. | |
| 6,294,222 B1 | 9/2001 | Cohen et al. | |
| 6,316,378 B1* | 11/2001 | Giebelhausen et al. | 502/10 |
| 6,376,404 B1* | 4/2002 | Giebelhausen et al. | 502/10 |
| 6,387,531 B1 | 5/2002 | Bi et al. | |
| 6,417,423 B1 | 7/2002 | Koper et al. | |
| 6,607,994 B2 | 8/2003 | Soane et al. | |
| 6,653,519 B2 | 11/2003 | Koper et al. | |
| 6,761,761 B1 | 7/2004 | Schilling et al. | |
| 6,827,766 B2 | 12/2004 | Carnes et al. | |
| 6,843,919 B2 | 1/2005 | Klabunde et al. | |
| 6,860,924 B2 | 3/2005 | Rajagopalan et al. | |
| 6,887,302 B2 | 5/2005 | Rajagopalan et al. | |
| 2002/0028333 A1 | 3/2002 | Giebelhausen et al. | |
| 2002/0035032 A1 | 3/2002 | Koper et al. | |
| 2002/0187258 A1 | 12/2002 | Bellemare et al. | |
| 2003/0013369 A1 | 1/2003 | Soane et al. | |
| 2003/0215355 A1 | 11/2003 | Lanz et al. | |
| 2003/0216256 A1 | 11/2003 | Axtell et al. | |
| 2004/0009726 A1 | 1/2004 | Axtell et al. | |
| 2005/0026778 A1 | 2/2005 | Axtell et al. | |

FOREIGN PATENT DOCUMENTS

JP 5131136 5/1993

OTHER PUBLICATIONS

Jaroniec et al. 'Comparison of Adsorption Methods for characterizing the Microporosity of Activated Carbons' in CARBON vol. 27 No. 1, pp. 77-83 1989.*

* cited by examiner

*Primary Examiner*—Stuart Hendrickson
(74) *Attorney, Agent, or Firm*—Keusey, Tutunjian & Bitetto, P.C.

(57) ABSTRACT

A reactive-adsorptive protective material having an activated carbon adsorbent, including those manufactured from a gel-type ion exchange resin. The activated carbon adsorbent has adsorptive properties for adsorbing chemical impurities. The activated carbon is wettlerized to further impart reactive properties onto the activated carbon for providing protection against blood agents in the atmosphere. Advantageously, a superior reactive-adsorptive material is provided having the ability to neutralize chemical substances, in particular, blood agents, while at the same time not diminishing the effectiveness of the carbon's adsorption capabilities.

22 Claims, 1 Drawing Sheet

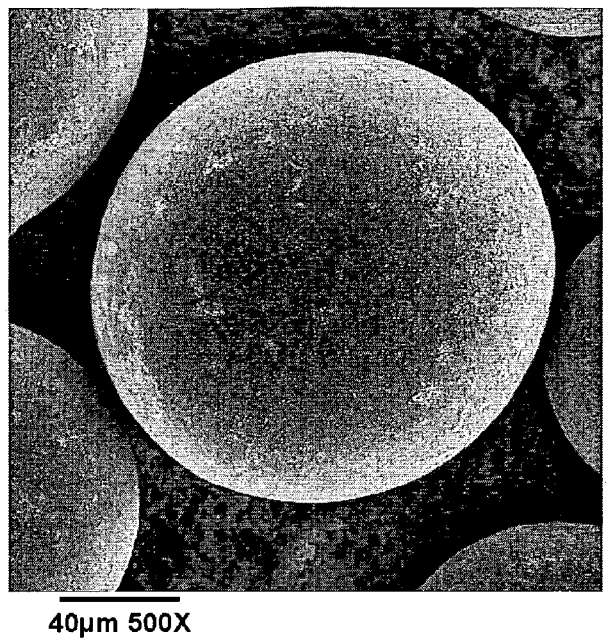
40μm 500X
FIG. 1-Untreated Ambersorb Carbon
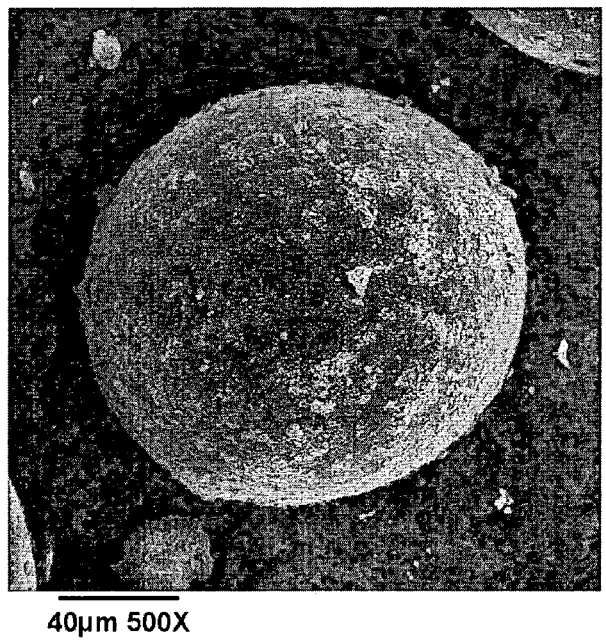
40μm 500X
Fig. 2 - Ambersorb Bead -- 1% treated MgO Nanoparticles

REACTIVE-ADSORPTIVE PROTECTIVE MATERIALS AND METHODS FOR USE

CROSS-REFERENCE TO RELATED APPLICATIONS

This utility application claims the priority date benefit of U.S. Provisional Application 60/360,050 filed on Feb. 25, 2002.

BACKGROUND OF THE INVENTION

1. Technical Field

The present invention relates generally to protective materials, and in particular, to reactive and adsorptive materials for providing protection from chemical agents and blood agents and methods for providing and using such materials. Also, these materials may be further treated to provide protection from biological agents.

2. Description of Related Art

Agents of chemical warfare have existed for a long time and can generally be grouped into the following three classes: 1) blister/percutaneous agents 2) nerve agents, and 3) blood agents.

1) Blister/percutaneous agents attack the skin and/or mucous membrane tissues external or internal, to the human body, including the inhalation route. The resulting blistering and ulceration is extremely debilitating and can be fatal. Typical of this class is Mustard (labeled as Agent HD) which can be present as a liquid or a gas or within an aerosolized carrier.

These agents were found early on to be readily adsorbed by activated carbon which, when contained within canister beds or immobilized/fixed within or upon various textile substrates, offered the ready capability to adsorb such agents and hold them away from vulnerable body areas of the person to be protected. Activated carbon has been made into and presented as powders, granules, dried slurries, fibers, spherical beads, etc. and is derived from a variety of processes which are performed on organic precursors such as coconut husks, wood, pitch and organic resins. Each process is unique but can be reduced in view to the following steps: (a) carbonizing the organic precursor material to carbon of modest internal surface area (of the order of tens to a few hundred of square meters or surface area per gram of carbon), and then (b) activating this carbon to produce a carbon with many hundreds to low thousands of $m^2/gm$ of surface area. Such activated carbon has strong adsorptive abilities. When a material adsorbs something, it means that it attaches to it by chemical attraction. The huge surface area of activated carbon gives it countless bonding sites. When certain chemicals pass next to the carbon surface they attach to the surface and are trapped.

The carbons materials must be fixed within or upon a carrier substrate in order to be rendered into a useful form. Such fixation, whether by way of adhesion or entrapment or some other mode of fixing the carbon on the carrier, must be done deftly enough such that as little as possible of the valuable surface area is obfuscated by the fixation process.

2) The nerve agents are a variety of compounds which can be presented as gases, liquids or secured either in aerosol or other carriers, much as is HD. They attack the human body and interfere with nervous system functioning via immobilization of key enzymes necessary therein, causing death or severe injury. They all operate principally via percutaneous and inhalation routes and are extremely toxic even in miniscule amounts. Typical of such species are Sarin and Soman, often referred to as the G agents (GB and GD). They are also efficiently adsorbed by carbon of high surface area with the same carbon source/process and fixation considerations as discussed above.

3) The blood agents are those species which, when inhaled, dissolve via the lungs in the blood and cause asphyxiation by displacing the oxygen ($O_2$) normally carried by the hemoglobin moieties with more potently binding species known as strong Lewis Bases. Such agents include Hydrogen Cyanide (HCN), Carbon Monoxide (CO), Phosgene ($COCl_2$) and others. The blood agents are minimally and essentially ignorably adsorbed by the activated carbon spoken of above. This is because the blood agents constitute molecules of too low a molecular weight such that their fugacity at normal temperatures exceeds any surface bonding power which the activated carbon can offer. Indeed, although activated carbon is useful for trapping carbon-based impurities ("organic" chemicals), as well as elements like chlorine, many other chemicals (sodium, nitrates, etc.) are not attracted to carbon at all, and therefore pass through unadsorbed. Thus, an activated carbon filter will remove only certain impurities while ignoring others.

It is to be noted that there are some chemical agents which can arguably be either percutaneous, inhalation or blood agents, or some combination of these simultaneously. However, for the purposes mentioned herein, such species would operationally fall into one or more of the modes of handling which are cited above.

Accordingly, there exists a need for materials which have improved adsorptive properties for greater adsorption of impurities and which also have reactive properties to concurrently and effectively neutralize chemical substances which, for example, cannot be adsorbed.

SUMMARY OF THE INVENTION

The present invention is directed to reactive and adsorptive materials for providing protection from chemical and/or biological agents and methods for providing such materials. Advantageously, the present invention provides for efficient and effective adsorption and neutralization of harmful chemical agents as well as blood agents.

Specifically, activated carbon according to the present invention advantageously retains an effective level of adsorptive ability (i.e., the surface area of the bead is not measurably diminished) despite being wettlerized (and/or imbedded with nanoparticles). This is so because even after being imbedded with metal ions and/or nanoparticles, an effective amount of pores in the activated carbon remain unoccluded such that the adsorptive properties of the carbon remain unaffected. This combination of features advantageously results in a superior reactive-adsorptive material having the ability to neutralize chemical substances and/or kill biological agents while at the same time not diminishing the effectiveness of the carbon's adsorptive capabilities.

According to an aspect of the present invention, a reactive-adsorptive protective material is provided comprising an activated carbon bead manufactured from a gel-type ion exchange resin, said activated carbon bead having pores for providing adsorptive properties, and metal ions infused into said pores of said activated carbon bead for imparting reactive properties onto the activated carbon.

According to yet another aspect of the present invention, a reactive-adsorptive protective material is provided comprising a gel-type ion exchange resin carbonized and activated to form activated carbon having adsorptive properties, pores within said carbon beads having a pore size distribution, and metal ions in contact with said pores, wherein the activated carbon retains an effective level of adsorptive ability.

According to yet another aspect of the present invention, a method of providing a reactive-adsorptive protective material is provided comprising the steps of producing activated carbon from a gel-type ion exchange resin, the activated carbon having adsorptive properties for adsorbing chemical impurities, and loading metal ions onto the activated carbon to further impart reactive properties onto the activated carbon for providing protection against blood agents which are in contact therewith.

According to another aspect of the present invention, the reactive-adsorptive materials according to the present invention may further be imparted with reactive biocidal nanoparticles, as per a process described in co-pending U.S. Patent Application entitled "Multi-Functional Protective Materials and Methods for Providing Same" filed on Feb. 23, 2003, bearing U.S. patent application Ser. No.10/372,527, entitled "Multi-Functional Protective Materials and Method for Use". The complete disclosure of this concurrently filed application is hereby incorporated by reference. For example, either an improved activated carbon bead according to the present invention by itself and/or an improved activated carbon bead that has been wettlerized can further be subjected to an electromagnetically induced impaction process in combination with simultaneous sieving so as to imbed nanoparticular agglomerated entities into the surface of the beads where they are held in place by the topographical imbedding in the carbon bead and the van der Waals forces between the particle ions and the carbon beads' surface/pore atoms proximate to the nanoparticle. Advantageously, these imbedded nanoparticles impart additional protection by destructively adsorbing chemicals and microorganisms. Specifically, the nanoparticles are able to protect against biological agents by destroying or inactivating microorganisms by attacking their cell membranes and oxidizing important functional proteins or DNA. The nanoparticle impaction process is further described in co-pending U.S. patent application Ser. No. 10/372,537.

These and other aspects, features and advantages of the present invention will be described or become apparent from the following detailed description of the preferred embodiments, which is to be read in connection with the accompanying drawings.

BRIEF DESCRIPTION OF THE DRAWINGS

FIG. 1 depicts an exemplary SEM micrograph of an untreated carbon bead.

FIG. 2 depicts an exemplary SEM micrograph of a carbon bead loaded with 1% MgO particles according to an aspect of the present invention.

DETAILED DESCRIPTION OF PREFERRED EMBODIMENTS

An activated carbonaceous bead with extraordinarily high surface area (e.g., ~1500 m²/gm) and extraordinary hardness (e.g., from about 2 to about 10 times harder than prior art Rohm & Haas and Kureha beads) comprises the activated carbon bead preferably used according to an aspect of the present invention. The materials and methods used for manufacturing the activated carbon bead used in the present invention are described in published U.S. Patent Application No. 2002-0028333 entitled "Spherical High Performance Adsorbents with Microstructure" by Giebelhausen et al. filed on Mar. 8, 2001, U.S. Pat. No. 6,376,404 entitled "Process for the Production of Shaped High-Performance Adsorbents" by Giebelhausen et al. filed on Mar. 15, 2000, and U.S. Pat. No. 6,316,378 entitled "Process for the Production of Shaped Activated Carbon" by Giebelhausen et al. filed on Mar. 15, 2000, the disclosures of which are all incorporated herein by reference thereto.

It is to be noted that the materials preferably used for manufacturing the activated carbon used according to the present invention preferably comprise spherical high-performance adsorbents which are manufactured from polymer resin by water vapor activation with an activation time of at least 6 hours. These adsorbents have a pronounced microstructure in the range of about 0 Å to about 40 Å pore diameter and an overall micropore volume of at least 0.6 $cm^3/g$. A substantial increase in the adsorption capacity for gases and vapors is achieved which is also represented by the very favorable ratio of weight capacity to volume capacity of up to 2 to 1. The spherical high-performance adsorbents with microstructure can be used for many purposes, in particular, textile fabrics for the adsorption of chemical warfare agents and toxic gases and vapors, in adsorption refrigerating plants in combination with the refrigerating agent methanol, in motor vehicle filters and biofilters.

As used in the claims, the term "activated carbon adsorbent" refers to any suitable form of activated carbon useful in protective applications. By way of non-limiting examples, the "activated carbon adsorbents" may take the form of beads, pellets, powders, granules, grains, tablets, particulates, fibers or dried slurries. A specific example having known utility is a bead having a highly uniform spherical shape. The spherical high-performance adsorbents preferably used in the present invention are explained in further detail below by means of exemplified embodiments.

EXAMPLE 1

Initially, 3 kg of a carbonized spherical cation exchanger polymer resin, sold under the designation Lewatit 1431, from Bayer AG, Leverkusen, having the following quality specification is selected as the starting material:

| | |
|---|---|
| Water content: | 1.1% |
| Volatile constituents: | 1.5% |
| Ash content: | 2.4% |
| Fixed carbon: | 96.1% |
| Sulphur content: | 15.0% |
| Granulation: | |
| >1.25 mm | 0.2% |
| 1.25 mm–1.0 mm | 5.1% |
| 1.0 mm–0.8 mm | 36.4% |
| 0.8 mm–0.5 mm | 56.1% |
| <0.5 mm | 2.2% |

These gel-type resin beads are discontinuously activated for 7 hours in an inert gas flow in an indirectly heated tubular rotary kiln, with the product being circulated 8 times per kiln rotation, with the addition of 0.75 kg/hr water vapor at a low pressure on the flue gas side of 0.1 mm water column and with a product temperature of 920° C., with respect to the overall heated kiln length.

A total water vapor quality of 0.75 kg/hr is metered into the activation kiln as follows:

| | |
|---|---|
| 0.11 kg/hr | water vapour over 17% of the kiln length |
| 0.15 kg/hr | water vapour over 43% of the kiln length |
| 0.23 kg/hr | water vapour over 54% of the kiln length |
| 0.15 kg/hr | water vapour over 65% of the kiln length |
| 0.11 kg/hr | water vapour over 83% of the kiln length |

The kiln length is measured from the bead input side. Then the produced high performance adsorbents are cooled and screened as grain fractions between 0.315 mm and 0.8 mm in size.

The spherical high-performance adsorbents used in the present invention have a microstructure which is characterized by the following pore distribution:

| pore diameter (in Å Angstrom) | pore volume (in cm²/g) | pore volume content of overall micropore micropore volumes (in %) |
|---|---|---|
| 40–20 | 0.031 | 5.0 |
| 20–10 | 0.114 | 18.7 |
| 10–8 | 0.09 | 14.8 |
| 8–5 | 0.249 | 40.8 |
| 5–0 | 0.126 | 20.7 |

The measurable dust content, i.e., grains smaller than 0.04 mm is less than 1%. The remaining grain-size distribution is as follows:

| | |
|---|---|
| 0.7–0.63 mm | 0.2% |
| 0.63–0.5 mm | 12.3% |
| 0.5–0.4 mm | 78.2% |
| 0.4–0.315 mm | 9.3% |

The spherical high-performance adsorbents used in the present invention are characterized by the following quality parameters specific to activated carbon:

| | | |
|---|---|---|
| Settled weight: | 585 | g/l |
| Ash | 1.9% | |
| Iodine value | 1388 | mg/g |
| Methylene blue | 28 | ml |
| BET surface | 1409 | m2/g |
| Breaking strength | 100% | |
| Dynamic hardness | 100% | |
| Abrasion strength | 100% | |
| Regeneration loss (after 10 regeneration cycles) | 1.5% | |

Then, 500 g of the spherical high-performance adsorbents according to the invention are applied to a textile fabric, so that a high packing density is produced with a single-layer covering. The efficiency of the high-performance adsorbents used is measured in comparison with a test substance (reference substance for chemical warfare agents) characterized by the adsorption speed constant in accordance with the formula:

$$\lambda = 2.3 \ldots \lg c_0/c_t \, a^{-1}$$

a=weight of adsorbent sample
$c_t$=concentration of the test substance after the adsorption time
$c_o$=initial concentration of the test substance
lg=logarithm The measurement results in comparison with reference products are given in Table 1:

TABLE 1

| Product | Adsorption speed constant λ |
|---|---|
| PAX 500[1] | 3.2 |
| HK 44[2] | 2.3 |
| Ambersorb 572[3] | 2.1 |

[1] PAK 500: sample of spherical high-performance adsorbents with microstructure
[2] HK 44: activated carbon on charcoal base
[3] Ambersorb 572: pyrolised ion exchanger resin from Rohm & Haas, USA

EXAMPLE 2

The suitability of the spherical high-performance adsorbents for biofilter installations is tested in a laboratory bioreactor. For this the product as given in Example 1 is filled into the reactor chamber and immobilized with microorganisms up to a charging of $3.7 \times 10^9$ cells/g base material. Then 20l/hr moist exhaust air with a toluene concentration of 500 mg/m³ are conveyed over the immobilized high-performance adsorbents. The achieved degradation capacity and the chamber charging with an efficiency of 90% are represented in Table 4.

TABLE 4

| Product | Degradation capacity (in g/m³ · h) | chamber charging at 90% efficiency (in g/m³ · h) |
|---|---|---|
| PAK 500[1] | 12.4 | 39.6 |
| WS IV[2] | 100.6 | 21.3 |
| C 40/3[3] | 74.5 | 14.5 |

[1] See Example 1
[2] WS IV: formed activated carbon (4 mm) on a charcoal base from Chemviron, Belgium
[3] C 40/3: formed activated carbon (3 mm) on a bituminous coal base according to the invention, CarboTex, Germany The infusion to varying degrees of prior art carbon with metal ions of the Transition Series in the Periodic Table is known. The metal ions can be introduced in a variety of modes such that the ions of the metals reside within the carbon (likely with the metal cations' charges balanced by nearby spectator gegenions such as oxide ($O^{-2}$)). It is likely that these metallic ions bind the blood agents via coordinate covalent ligand bonds. The metal ions are strong Lewis acids—electron acceptors; while the agents are strong Lewis bases—electron donors called ligands. When these two encounter each other they bind strongly.

In addition, some blood agents are bound temporarily and then decompose to species which become the bound ligands or which can be adsorbed by the carbon. The process by which carbon is perfused/infused with these metal ions is known somewhat generically as "wettlerizing" and originally used ionic species including ions of Chromium and Cadmium. With the recognition over time that some of those metals were carcinogenic to varying degrees, the metal mix presently used has preferably changed to include ions of zinc, copper, molybdenum and others, while excluding the more toxic metals. As used in the claims, the term "loaded" means a perfusion process or an infusion process or a wettlerization process to place metal ions on an activated carbon adsorbent without affecting the adsorbent's ability to combat an adsorbable chemical threat.

The activated carbon beads used in the present invention are preferably further subjected to a wettlerization process to infuse the proper transition metal ions into place within/onto the carbon beads. Advantageously, the activated carbonaceous bead preferably used according to an aspect of the present invention has, as described above, both an extraordinarily high surface area (e.g., about 1500 $m^2$/gm) and extraordinary hardness (e.g., from about 2 to about 10 times harder than Rohm & Haas and Kureha beads). These carbon beads have the ability and capacity to take up these metallic ions well in excess of previously tried carbon beads of the prior art (e.g., Rohm & Haas and Kureha) while at the same time not measurably diminishing either the surface area of the bead or its hardness. Specifically, activated carbon according to the present invention advantageously retains an effective level of adsorptive ability (i.e., the surface area of the bead is not measurably diminished) despite being wettlerized (and/or imbedded with nanoparticles). This is so because even after being imbedded with metal ions and/or nanoparticles, an effective amount of pores in the activated carbon remain unoccluded such that the adsorptive properties of the carbon remain unaffected. This combination of features advantageously results in a superior reactive-adsorptive material having the ability to neutralize chemical substances and/or kill biological agents while at the same time not diminishing the effectiveness of the carbon's adsorptive capabilities.

Thus, a metal-ion-treated carbon bead according to the present invention comprises a highly adsorptive bead which can also react with and neutralize blood agents. Advantageously, the unique surface area and pore distribution at the surface and within the bead provide a hybrid product having unexpected, novel, useful and unique abilities and very desirable properties. In particular, the unique pore distribution of the carbon bead used according to the present invention results in an especially effective overall resultant product having an improved range of protective properties. Specifically, the resultant product comprises a material having both reactive properties for reacting with and/or neutralizing chemical substances (e.g., blood agents) as well adsorptive properties for adsorbing chemical impurities. This reactive-adsorptive material preferably comprises an activated carbon bead manufactured from a gel-type ion exchange resin, wherein the bead is preferably further subjected to a wettlerization process for introducing metal ions within and onto the carbon bead to impart the reactive properties to the bead.

Whether the threat is chemical or biological and whether it is presented as a liquid or a gas, the barrier which physically and chemically protects the user (e.g., clothing, mask, filter, etc.) is subjected to the following processes when in use:

(1) Molecules of gaseous chemical agent diffusing through the barrier at some characteristic rate.
(2) Liquid droplets of chemical agent diffusing unaided or aided by some external pressure through the barrier at some characteristic rate.
(3) Biological aerosolized microdroplets diffusing at some characteristic rate through the barrier.
(4) Carbon physically adsorbing organic entities at some characteristic rate of adsorption.
(5) Iodinated resins or Nanoparticular entities reacting with biological entities and their toxic residues in the latter case at characteristic rates of reaction.
(6) Entities within carbon reacting with the very fugitive blood agents at some characteristic chemical rate of reaction.
(7) Normal safe air ($O_2$ and $N_2$, for all practical purposes) and water vapor diffusing through the barrier at their characteristic diffusion rates.

An ideal response to a chemical/biological threat is to minimize (1), (2), and (3) while maximizing (4) through (7). However, since these processes are coupled to each other, any modestly successful approach walks a fine line to meet these criteria.

It is to be noted that the reactive-adsorptive materials according to the present invention may further be imparted with reactive biocidal nanoparticles, as per a process described in co-pending U.S. patent application Ser. No. 10/372,537 entitled "Multi-Functional Protective Materials and Methods for Use." For example, either an improved activated carbon bead according to the present invention by itself as well as an improved activated carbon bead that has been wettlerized can further be subjected to an electromagnetically induced impaction process in combination with simultaneous sieving so as to imbed nanoparticular agglomerated entities into the surface of the beads where they are held in place by the topographical imbedding in the carbon bead and the van der Waals forces between the particle ions and the carbon beads' surface/pore atoms proximate to the nanoparticle. Advantageously, these imbedded nanoparticles impart additional protection by destructively adsorbing chemicals and microorganisms. Specifically, the nanoparticles are able to protect against biological agents by destroying or inactivating microorganisms by attacking their cell membranes and oxidizing important functional proteins or DNA. The process by which the nanoparticles are loaded onto the carbon is an electromagnetically assisted impact collision (MAIC) process which is further described in co-pending U.S. patent application Ser. No. 10/372,537 mentioned above.

The nanoparticles preferably comprise environmentally stable nanometer-sized clusters of atoms and molecules having high surface areas and unique morphologies which result in high chemical reactivity. The reactive/adsorptive particulates used according to the present invention are preferably inorganic, reactive nanoparticulates formed from about 1 nm to about 200 nm sized clusters.

Reactive nanoparticles used for protective applications are specifically engineered to destructively adsorb chemicals and microorganisms. Specifically, a nanoparticle adsorbs then detoxifies hazardous chemicals by breaking molecular bonds to yield harmless end products. Similarly, the reactive/adsorptive nanoparticles are able to kill or inactivate a microorganism by attacking its cell membrane and oxidizing important functional proteins or DNA.

Exemplary nanoparticles which may be used include metal oxide composites in powder nanoparticulate form. These metal oxide composites comprise metal oxide nanoparticles having oxygen ion moieties on their surfaces with reactive atoms interacted or chemisorbed with those surface oxygen ions. For example, the metal oxide nanoparticles may be taken from the group consisting of oxides of Mg, Ti, Ca, Al, Sn, Fe, Co, V, Mn, Ni, Cr, Cu, Zn, Zr, or mixtures thereof. For example, the metal oxide nanoparticles may comprise $MgO$, $TiO_2$, $CaO$, $Al_2O_3$, $SnO_2$, $Fe_2O_3$, $FeO$, $CoO$, $V_2O_5$, $MnO_3$, $NiO$, $Cr_2O_3$, $CuO$, $ZnO$, $ZrO_2$ and mixtures thereof. Nanoparticles made of metal complexes of hydroxides, metal complexes of hydrates as well as polyoxometallates (POMs) are also suitable. Some of the nanoparticles listed in this paragraph may also be further processed, for example to include reactive halogen atoms, alkali metal atoms, a metal nitrate, $SO_2$, $NO_2$, ozone or a second different metal oxide. Alternate processing can provide a protective coating to the nanoparticles which are not soluble rendering them waterproof. These advanced processing steps are disclosed in the following U.S. Pat. Nos. 6,057,488 and 5,914,436 and 5,990,373 and 5,712,219 and 6,087,294 and 6,093,236 and 5,759,939 and 6,417,423 and in Published U.S. Patent Application 2002/0035032, the complete disclosures of which are incorporated herein by reference thereto. Any of these products may be incorporated into the multi-functional protective products according to the invention.

The reactive/adsorbent nanoparticulates are thus advantageously capable of:

a) Breaking down, decomposing or neutralizing chemicals (e.g. reactive/adsorptive nanoparticulates)

b) Acting as a biocide, killing microorganisms c) Neutralizing chemicals and simultaneously acting as a biocide (e.g. reactive/adsorptive nanoparticulates such as MgO nanoparticles, etc.). These nanoparticles may be enhanced or modified for environmental purposes.

Thus, the nanoparticles preferably used according to the present invention include at least one of chemically adsorptive nanoparticles, chemically reactive nanoparticles, and biocidally reactive nanoparticles. Further, the nanoparticles used according to the present invention preferably have a Brunauer-Emmett-Teller (BET) multi-point surface area of at least about 70 $m^2/g$ for older nanoparticles to at least about 1200 $m^2/g$ or more for more advanced nanoparticles and have an average pore radius of at least about 45 Angstroms to at least about 100 Angstroms.

In one example, Magnesium Oxide (MgO) nanoparticles in concentrations of 0.5, 1.0 and 2.0% by weight were loaded onto Ambersorb R-1500 carbon beads (produced by Rohm & Haas). For comparative purposes and for use as a control, Ambersorb carbon was processed in the MAIC system without the addition of nanoparticles. Visual observations of the treated samples indicated good attachment and distribution of the MgO on the Ambersorb carbon. FIG. 1 depicts an exemplary SEM micrograph of an untreated Ambersorb bead. FIG. 2 depicts an exemplary SEM micrograph of an Ambersorb bead loaded with 1% MgO nanoparticles according to an aspect of the present invention. This resultant treated particle illustrated in FIG. 2 has the appearance of a spherical "cookie" with "raisins" in its surface partially imbedded and partly exposed.

The nanoparticles used in accordance with the invention are those that possess a protective property, i.e. protective nanoparticles or protective nanoparticulate entities. For purposes of this application, the term "protective nanoparticles" encompasses one or more of the following three particular types of nanoparticles: chemically adsorptive nanoparticles; chemically reactive nanoparticles; and biocidally reactive nanoparticles.

Protective nanoparticles are metal-containing nanoparticles or metal-containing nanocrystals. The metals are present as metal oxides, metal hydroxides, metal hydrates, POMs. To enhance their protective properties, such metal-containing protectants may be combined with one of more of a metal oxide, Group I metals, Group IA metals, a reactive halogen, a metal nitrate, $SO_2$, $NO_2$, or ozone.

It should be noted that a bulk metal-containing particle that is ground down to a powder will not possess the protective properties of the nanoparticles used according to the invention because the ground powder will have conventional surface features. In order to distinguish powders from nanoparticles which may be seemingly in the same size range, the protectants according to the invention are referred to as finely divided nanoparticles or finely divided nanocrystals. Protective nanoparticles are formed from 1 nm to 200 nm sized nanoparticulate clusters. These clusters cling together due to van der Waals forces and therefore have many distinguishable constituent parts. A ground powder is just a single entity, with a uniform exterior surface. In contrast thereto, when the nanometer sized clusters cling together much of their original surface area is preserved providing Brunauer-Emmett-Teller (BET) multi-point surface areas of at least 70 $m^2/g$ for early protective nanoparticles and surface areas of at least 1200 $m^2/g$ for later versions. These surfaces may contain pores having an average pore radius from 45 Angstroms to 100 Angstroms.

While the structure, surface area and pore size have imbued the nanoparticles with their protective properties, these structural features have also interfered with past attempts to incorporate the nanoparticles into tangible protective filter precursors. Failed attempts have resulted from an inability to control the van der Waals forces resulting in excessive clumping or from an inability to control the adhesive or retaining means resulting in occluding of useful surface areas or pores. The invention is concerned with products and methods that utilize nanoparticles in a flexible manner to readily incorporate one or more of their chemically adsorptive, chemically reactive or biocidally reactive properties.

Although illustrative embodiments of the present invention have been described herein, it is to be understood that the present invention is not limited to those precise embodiments, and that various other changes and modifications may be affected therein by one skilled in the art without departing from the scope or spirit of the present invention. For example, it is expressly intended that all combinations of those carbon beads, metal ions and/or method steps and/or substrate materials which perform substantially the same function in substantially the same way to achieve the same results are within the scope of the invention. Moreover, it should be recognized that any disclosed form or embodiment of the invention may be incorporated in any other disclosed or described or suggested form or as a general matter of compatibility of application method. It is the intention, therefore, to be limited only as indicated by the scope of the claims appended hereto.

What is claimed is:

1. A method of providing a reactive-adsorptive protective material comprising the steps of:

producing activated carbon having a BET surface area on the order of 1500 $m^2/g$ for providing adsorptive properties and a pore size distribution having about 80% of the pores below 40 Å; and loading metal ions onto the activated carbon to further impart reactive properties onto the activated carbon for providing protection against blood agents which are in contact therewith, wherein the pore size distribution results in metallic ion take up without measurably diminishing the surface area;

impacting finely-divided inorganic metal oxide nanocrystals onto said activated carbon to topographically imbed the nanocrystals to provide chemical or biocidal protection.

2. The method of claim 1, wherein said loading step comprises infusing metallic salts.

3. The method of claim 1, wherein said loading step comprises perfusing metallic salts.

4. The method of claim 1, wherein said loading step compnses wettlerizing metallic salts.

5. The method of claim 1, wherein said activated carbon has a microstructure with pores in a size range between 0 Å and 40 Å, wherein 5% to 10% of the overall micropore volume includes pores between 20-40 Å;
15% to 25% of the overall micropore volume includes pores between 10-20 Å;
10% to 20% of the overall micropore volume includes pores between 8-10 Å;
40% and 50% of the overall micropore volume includes pores between 5-8 Å; and
10%-25% of the overall micropore volume includes pores smaller than 5 Å.

6. The method of claim 1, wherein said loaded metal ions are selected from the group consisting of zinc, copper and molybdenum.

7. The method of claim 1, wherein the activated carbon bead is produced by:
delivering a gel-type ion exchange resin to a rotary tunnel dryer pre-heated to from 880° to 900° C. up to a filling volume of from 10 to 20%, wherein a product temperature of from 250° to 300° C. is set up in the dryer in the 50 to 80% kiln length range, said kiln length range being calculated from the product input;
drying the gel-type ion exchange resin continuously with 6-fold product turnover per kiln rotation and a residence time of from 30 to 60 minutes by means of a hot gas in countercurrent to a residual moisture content of at least 10%;
transferring the gel-type ion exchange resin to an indirectly heated rotary tunnel kiln up to a filling volume of from 5 to 10%, said indirectly heated rotary tunnel kiln having a carbonizing zone and an activating zone, wherein the gel-type ion exchange resin is carbonized and activated continuously in an inert-gas flow with 8-fold product turnover per kiln rotation and with a product temperature profile in the carbonizing zone of from 850° to 900° C. and a residence time of from 120 to 180 minutes, and with a product temperature profile in the activating zone of from 910° to 920° C. and a residence time of from 480 to 720 minutes with the addition of from 3 to 5 kg/h.kg of steam in the activating zone.

8. The method of claim 7, wherein the flow-rate of the hot gas in the dryer, expressed in terms of free cross-section, is from 0.2 to 0.5 m/s, with a kiln length to kiln diameter ratio of from 5.5 to 10.

9. The method of claim 7, wherein the carbonizing zone covers 20% and the activating zone covers 80% of the heated kiln length, calculated from the product input.

10. The method of claim 7, wherein the carbonizing takes place with a product temperature profile, calculated in terms of the heated kiln length from the product input, of 850° C. at the product input, 880° C. after 10% of the kiln length and 900° C. after 20% of the kiln length.

11. The method of claim 7, wherein the activation takes place with a product temperature profile, calculated in terms of the heated kiln length from the product input, of 910° C. after 30% of the kiln length, 920° C. after from 40 to 70% of the kiln length, 915 C after 80% of the kiln length and 910° C. at the product output.

12. The method of claim 1, wherein said loaded metal ions are adapted to strongly bond with blood agents selected from the group consisting of hydrogen cyanide, carbon monoxide and phosgene.

13. The method of claim 1, wherein said impacting step comprises electromagnetically impacting the nanocrystals into the activated carbon.

14. The method of claim 13, further comprising the step of sieving the protective nanocrystals during said impacting step.

15. The method of claim 1, wherein said nanocrystals have oxygen moieties on their surfaces so that chemical agent threats are adapted to be reacted or chemisorbed with said surface oxygen moieties.

16. The method of claim 1, further comprising the step of sieving the protective nanoparticles during said impacting step.

17. The method of claim 1, wherein said nanocrystals are selected from the group consisting of chemically adsorptive nanocrystals, chemically reactive nanocrystals, biocidally reactive nanocrystals, and combinations thereof.

18. The method of claim 1, wherein said nanocrystals are selected from the group consisting of metal oxides, metal hydroxides, metal hydrates, POMs, and combinations thereof.

19. The method of claim 1, wherein said nanocrystals are combined with a material selected from the group consisting of a metal oxide, a reactive halogen, an alkali metal, a metal nitrate, $SO_2$, $NO_2$, ozone and combinations thereof.

20. The method of claim 1, wherein said nanocrystals are formed from 1-200 nm sized nanoparticle clusters.

21. The method of claim 1, where said nanocrystals have a Brunauer-Emmett-Teller (BET) multi-point surface area of at least about 70 $m^2/g$ to at least about 120 $m^2/g$.

22. The method of claim 1, wherein said nanocrystals have an average pore radius of at least about 45 Angstroms to at least about 100 Angstroms.

* * * * *